US011142738B2

(12) United States Patent
Kulinsky

(10) Patent No.: US 11,142,738 B2
(45) Date of Patent: Oct. 12, 2021

(54) SIEVE SYSTEM AND METHODS FOR CELL MEDIA EXCHANGE

(71) Applicant: The Regents of the University of California, Oakland, CA (US)

(72) Inventor: Lawrence Kulinsky, Irvine, CA (US)

(73) Assignee: THE REGENTS OF THE UNIVERSITY OF CALIFORNIA, Oakland, CA (US)

(*) Notice: Subject to any disclaimer, the term of this patent is extended or adjusted under 35 U.S.C. 154(b) by 163 days.

(21) Appl. No.: 15/719,180

(22) Filed: Sep. 28, 2017

(65) Prior Publication Data

US 2018/0112170 A1  Apr. 26, 2018

Related U.S. Application Data

(60) Provisional application No. 62/412,722, filed on Oct. 25, 2016.

(51) Int. Cl.
*C12M 1/00* (2006.01)
*C12M 1/12* (2006.01)

(52) U.S. Cl.
CPC ............ *C12M 25/04* (2013.01); *C12M 23/50* (2013.01); *C12M 29/04* (2013.01)

(58) Field of Classification Search
CPC ....... C12M 23/50; C12M 25/04; C12M 29/04
USPC ................................ 435/287.1, 289.1, 297.5
See application file for complete search history.

(56) References Cited

U.S. PATENT DOCUMENTS

| 5,578,490 A * | 11/1996 | Martinez Ubeira ... C12M 23/12 422/504 |
| 6,284,113 B1 * | 9/2001 | Bjornson ............. B01J 19/0046 204/450 |
| 2013/0029412 A1 * | 1/2013 | Reis ....................... C12M 25/04 435/325 |
| 2014/0196550 A1 * | 7/2014 | Chernomorsky ...... C12M 23/12 73/864.91 |

FOREIGN PATENT DOCUMENTS

| ES | 2358699 A1 * | 5/2011 | ............ B01L 3/5025 |
| JP | 2002125656 A * | 5/2002 | ............ C12M 23/12 |
| WO | WO-02097029 A2 * | 12/2002 | ............ B01L 3/5025 |

OTHER PUBLICATIONS

Cho et al., "English-machine translation of JP-2002125656-A." (Year: 2002).*

* cited by examiner

*Primary Examiner* — Liban M Hassan
(74) *Attorney, Agent, or Firm* — Nguyen Tarbet LLC

(57) ABSTRACT

Methods and systems for cell media exchange wherein media maybe aspirated without also aspirating cells and wherein removal and re-plating of cells is not necessarily required. For example, the cell culture system or apparatus features a gap that is small enough to retain cells therein and also sized to prevent media from leaking. The methods and systems of the present invention may help reduce stress and damage to cells as compared to traditional methods that require removing and re-plating cells.

6 Claims, 2 Drawing Sheets

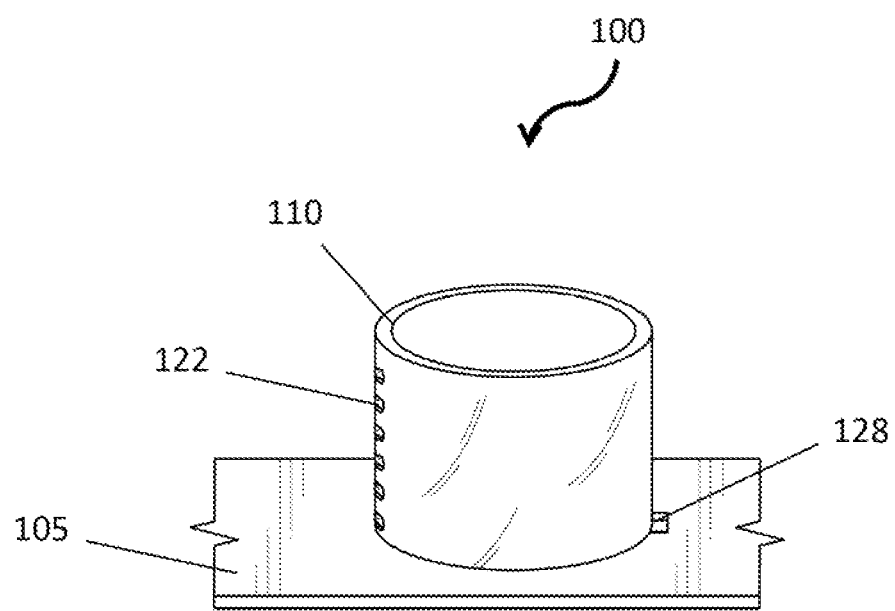
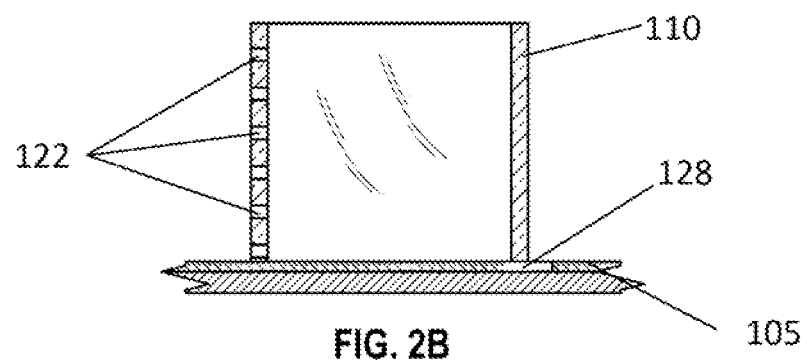

SIEVE SYSTEM AND METHODS FOR CELL MEDIA EXCHANGE

CROSS REFERENCE

This application claims priority to U.S. Provisional Patent Application No. 62/412,722 filed Oct. 25, 2016, the specification(s) of which is/are incorporated herein in their entirety by reference.

FIELD OF THE INVENTION

The present invention relates to devices and methods for changing media for cells in cell culture, more particularly to methods and systems featuring a cell culture dish that allows for aspiration of media without contact with the cells in culture.

BACKGROUND OF THE INVENTION

In order to grow cells of all types, including embryos, media that contains nutrients and growth factors is usually regularly changed, e.g., the old media is removed and new media (e.g., new type of media, same type of media) replaces the old. Typically, media exchange involves pipetting cells out of the dish and placing them in a new dish with the new media. This process of cell handling is stressful for cells, and it always possible to damage the cells during the transfer. Alternatively, media may be aspirated and new media may be added. With this method, there is always a danger of aspirating the cells along with the media.

The present invention features methods and systems for cell media exchange, wherein media may be safely aspirated from the dish. For example, the present invention features a cell culture apparatus (e.g., cell culture dish, well, well, etc.) wherein media can be aspirated therefrom via a gap that is small enough to retain cells therein and also sized to prevent media from leaking (e.g., via surface tension). Since media can be aspirated from the gap, there is typically not a need to handle the cells in a similar fashion as described above for previous methods; thus, the methods and systems of the present invention can help reduce stress and damage to cells.

SUMMARY OF THE INVENTION

The present invention features a cell culture sieve system that allows media exchange without having to remove the cells. In some embodiments, the cell culture sieve system comprises a cell culture container adapted to grow or sustain cells in culture, wherein a gap is disposed in the container. The gap is sized and adapted to retain media in the container in the absence of suction and to allow aspiration of the media in the presence of suction.

For example, the present invention features a cell culture sieve system comprising a well atop a culture substrate forming a container for holding media and cells in culture, wherein a gap is disposed in the well, the gap is sized to retain media in the well when suction is not applied to the gap and to allow aspiration of said media from the well when suction is applied to the gap. The gap is sized to retain cells in the well when suction is applied to the gap.

The size of the gap may be chosen based on the size of the cells to be contained. For example, the gap is smaller than the size of the cells. Surface tension may help prevent media from leaking through the gap. In some embodiments, the gap is from 0.05 microns to 100 microns at its largest dimension. In some embodiments, the gap is 0.05, 0.1, 1, 10, 20, 30, 40, 50, 60, 70, 80, 90, or 100 microns at its largest dimension. In some embodiments, the gap is from 0.05 to 10 microns, 10 to 50 microns, or 50 to 100 microns at its largest dimension. In some embodiments, the gap is greater than 100 microns at its largest dimension. (In some embodiments, the largest dimension is diameter.)

In some embodiments, the gap is disposed at an intersection of the culture substrate and the well.

In some embodiments, the system further comprises an outer wall surrounding the well and spaced a distance apart from the well. In some embodiments, the system further comprises a pipet placement area disposed in the culture substrate at the gap, the pipet placement area allows for aligning a pipet tip with a gap. In some embodiments, the culture substrate is a part of a slide or plate. In some embodiments, the cell culture sieve system is part of a multi-well cell culture plate. In some embodiments, the well is attached or connected to the culture substrate via an adhesive. In some embodiments, the gap is a cut or hole in the adhesive.

In some embodiments, the system comprises a slot disposed in the culture substrate intersecting with the gap and fluidly connected to the gap. In some embodiments, the slot is a cut or hole in an adhesive connecting the well to the culture substrate. In some embodiments, both the gap and the slot are cuts or holes in the adhesive.

In some embodiments, the system comprises a plurality of gaps extending from at or near a bottom edge of the well and upwardly toward a top edge (e.g., to the top edge, to the middle, to a place near the top edge, etc.) of the well.

The present invention also features a method of aspirating cell culture media (or a method of changing cell culture media). In some embodiments, the method comprises applying suction to a gap in a cell culture sieve system of the present invention, wherein suction applied to the gap removes media but not cells from the well of the cell culture sieve system. In some embodiments, applying suction to the gap comprises using a pipet to aspirate media through the gap. In some embodiments, the method is manual. In some embodiments, the method is automated. In some embodiments, the method further comprises adding new media to the well of the cell culture sieve system.

Without wishing to limit the present invention to any theory or mechanism, it is believed that the methods and systems of the present invention are advantageous because they allow the exchange of media in the same cell reservoir yet there is little or no aspiration of cells during the aspiration process. Further, the media exchange process can be accomplished without physically contacting the cells, thereby avoiding the physical stress associated with re-plating of cells.

Any feature or combination of features described herein are included within the scope of the present invention provided that the features included in any such combination are not mutually inconsistent as will be apparent from the context, this specification, and the knowledge of one of ordinary skill in the art. Additional advantages and aspects of the present invention are apparent in the following detailed description and claims.

BRIEF DESCRIPTION OF THE DRAWINGS

The features and advantages of the present invention will become apparent from a consideration of the following detailed description presented in connection with the accompanying drawings in which:

FIG. 2A shows a perspective view of a sieve system of the present invention. Gaps are disposed in the well, and a slot is present between the bottom of the well and the cell culture substrate. The present invention is not limited to the configuration shown in FIG. 2A.

FIG. 2B shows a cross sectional view of the system of FIG. 2A. Note the present invention is not limited to the configuration shown in FIG. 2B.

DETAILED DESCRIPTION OF THE INVENTION

Following is a list of elements corresponding to a particular element referred to herein:
100 sieve system
102 media (e.g., with cells)
105 cell culture substrate (e.g., plate, etc.)
110 well
122 gap
128 slot (e.g., pipet placement area)

The present invention cell culture sieve systems and methods for media exchange featuring a cell culture dish that allows for aspiration of media without contact with the cells in culture.

Figure 1A:
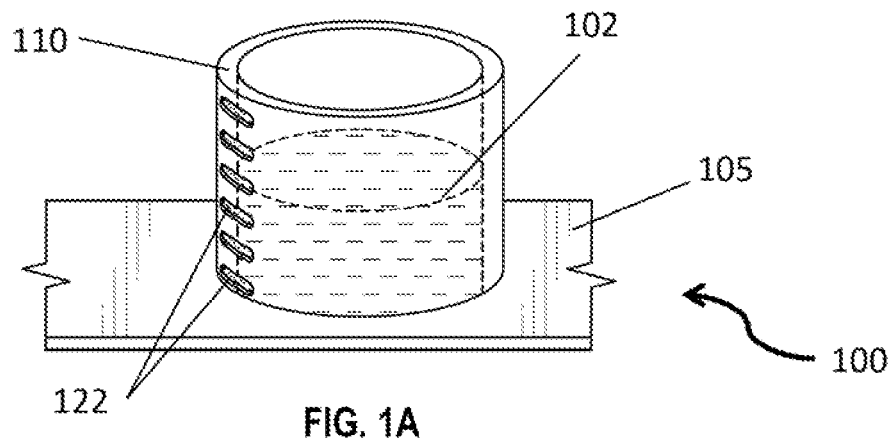
FIG. 1A shows a perspective view of a sieve system of the present invention comprising several gaps (the gaps are for media aspiration). The present invention is not limited to the configuration shown in FIG. 1A.
Figure 1B:
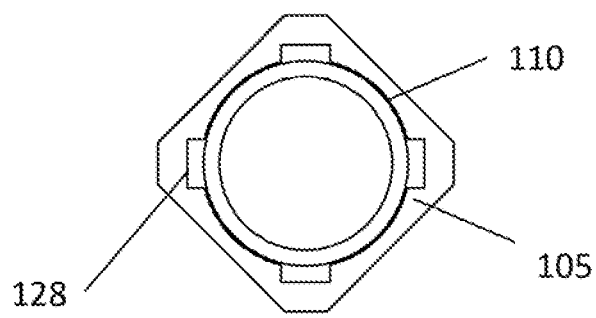
FIG. 1B shows a top view of a sieve system of the present invention wherein slots are present between the bottom of the well and the cell culture substrate (the slots are for media aspiration). The present invention is not limited to the configuration shown in FIG. 1B.
Figure 1C:
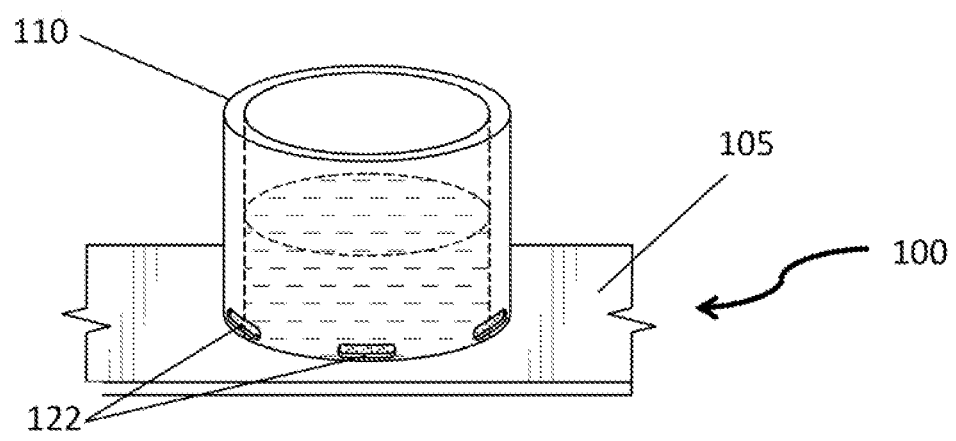
FIG. 1C shows a perspective view of a sieve system of the present invention comprising several gaps along the bottom edge of the well (the gaps are for media aspiration). The present invention is not limited to the configuration shown in FIG. 1C.

Referring to FIG. 1A, FIG. 1B, and FIG. 1C, the sieve system (100) of the present invention comprises a well (110) adapted to hold media (102), e.g., media with cells. The well (110) may be a part of a cell culture substrate (105), e.g., a dish, e.g., a single dish, a multi-well dish, a plate, etc., or any other appropriate cell culture mechanism. Note in FIG. 1A and FIG. 1C, the culture substrate (105) resembles a plate or a strip. The present invention is not limited to this configuration.

In some embodiments, the well (110) is mounted or connected to the cell culture dish via an adhesive, e.g., a double-sided adhesive. The present invention is not limited to this construction. For example, the well (110) may be constructed as a single unit (e.g., via injection molding or other processes), e.g., the well has a base floor or is directly constructed on the cell culture dish).

One or more gaps (122) are disposed in the well (110). The gaps (122) are for aspirating media. For example, as shown in FIG. 1A, FIG. 2A, and FIG. 2B, gaps are disposed at the intersection of the bottom of the well (110) and the cell culture substrate (105), as well as in locations higher up toward the top of the well (110). A user may choose a gap from which media is to be aspirated. FIG. 1C shows several caps along the bottom edge of the well (110).

The gaps (122) are sufficiently small enough that media will not leak out (e.g., via surface tension), but the gaps (122) allow aspiration of the media via suction. The gaps (122) provide size selection. For example, the gaps (122) are sufficiently small enough such that cells will not be aspirated when suction is applied to the gaps (122) (e.g., to remove the media). Thus, a gap size may be chosen based on the size of a cell of interest. For example, if the cell of interest were approximately 100 microns in diameter, a gap of less than 100 microns (e.g., 70 microns) would be selected. If the cell was 10 microns in diameter, a gap of less than 10 microns (e.g., 5 microns) may be chosen.

In some embodiments, the gap (122) is from 0.5 microns to 100 microns at its largest dimension (e.g., diameter). In some embodiments, the gap (122) is 0.05 microns, 1 micron, 5 microns, 10 microns, 20 microns, 30 microns, 40 microns, 50 microns, 60 microns, 70 microns, 80 microns, 90 microns, or 100 microns at its largest dimension (e.g., diameter). In some embodiments, the gap is from 0.05 to 10 microns at its largest dimension (e.g., diameter). In some embodiments, the gap is from 1 to 10 microns at its largest dimension (e.g., diameter). In some embodiments, the gap is from 10 to 50 microns at its largest dimension (e.g., diameter). In some embodiments, the gap is from 50 to 100 microns (e.g., 70-75 microns) at its largest dimension (e.g., diameter). In some embodiments, the gaps (122) are less than 100 microns at its largest dimension (e.g., diameter). In some embodiments, the gaps (122) are more than 100 microns at its largest dimension (e.g., diameter).

As shown in FIG. 1B, FIG. 2A and FIG. 2B, in some embodiments, the system (100) comprises slots (128) (or pipet placement areas), e.g., slots in between the well (110) and the culture substrate (105). The slots (128) may be places where a pipet tip is placed so media can be extracted. The slots (128) are similar to the gaps (122) in terms of size and function.

In some embodiments, an inner wall is disposed in the well (not shown), e.g., an inner wall forming an enclosure. The inner wall may be very short in height, e.g., about the height of a cell (e.g., 10-15 um, 15-20 um, 20-30 um, etc. The inner wall may be for helping to enclose the cells or sequester the cells in a particular area on the cell culture substrate (105) within the well (110).

The present invention described herein uses specially designed cell wells (e.g., wells, beakers, etc.) that allow media exchange to take place with cells remaining in the same beaker and where these cells are not contacted during this media exchange. In some embodiments, when the media needs to be exchanged, a pipette tip is placed outside the gap (122) and the old media is aspirated. In some embodiments, the gap (122) is disposed in the double-sided adhesive (120). The present invention is not limited to the user of double sided adhesive. For example, the gap (122) may be disposed in the well or other component of the system. The suction force is stronger than the capillary surface tension holding the media in the well and the media can be evacuated, while the cells stay in the well due to size exclusion principle, as their size is larger than the gap size. FIG. 5 shows a system after aspiration, wherein 100-micron polystyrene beads remain (have not been aspirated). FIG. 6 shows that the beads are not sucked into the aspiration media.

The system of the present invention may feature a slightly hydrophobic surface that will not allow fluid (e.g., media) to escape through the gap. For example, in some embodiments, the material used to form the system or components thereof (e.g., the gap) may be chosen to be slightly hydrophobic (e.g., a plastic). In some embodiments, the material is hydrophilic but is coated (or a portion is coated, e.g., the gap) to be slightly hydrophobic. In some embodiments, the gap may be slightly hydrophilic so as to allow fluid to go through but only to form a droplet just outside of the gap (so fluid doesn't escape further).

In some embodiments, the media exchange is manual. In some embodiments, the media exchange is automated.

Various modifications of the invention, in addition to those described herein, will be apparent to those skilled in the art from the foregoing description. Such modifications are also intended to fall within the scope of the appended claims. Each reference cited in the present application is incorporated herein by reference in its entirety.

Although there has been shown and described the preferred embodiment of the present invention, it will be readily apparent to those skilled in the art that modifications may be made thereto which do not exceed the scope of the appended claims. Therefore, the scope of the invention is only to be limited by the following claims. Reference numbers recited in the claims are exemplary and for ease of review by the patent office only, and are not limiting in any way. In some embodiments, the figures presented in this patent application are drawn to scale, including the angles, ratios of dimensions, etc. In some embodiments, the figures are representative only and the claims are not limited by the dimensions of the figures. In some embodiments, descriptions of the inventions described herein using the phrase "comprising" includes embodiments that could be described as "consisting of", and as such the written description requirement for claiming one or more embodiments of the present invention using the phrase "consisting of" is met.

The reference numbers recited in the below claims are solely for ease of examination of this patent application, and are exemplary, and are not intended in any way to limit the scope of the claims to the particular features having the corresponding reference numbers in the drawings.

What is claimed is:

1. A cell culture sieve system (100) comprising a culture substrate (105) and a side wall (110) disposed atop the culture substrate (105) to form a container for holding media and cells in culture, wherein the side wall has at least one gap (122) disposed therein, wherein the at least one gap (122) directly connects the container with an exterior of the cell culture system, at least one slot (128) is disposed between a bottom of the side wall and the culture substrate, wherein the at least one slot (128) is a cut or hole in an adhesive connecting the sidewall to the culture substrate, wherein the at least one slot (128) is sized and configured to receive a pipette tip, wherein the at least one gap (122) and the at least one slot (128) are configured to retain media via surface tension and to prevent media from leaking from the container, wherein when suction is applied to the at least one slot (128) or the at least one gap (122), media is aspirated from the container via the at least one slot (128) or the at least one gap (122), wherein the at least one gap (122) and the at least one slot (128) are sized and configured to prevent cells within the container from exiting the container, and wherein the at least one gap (122) forms an interface between the media within the container and air.

2. The cell culture sieve system (100) of claim 1, wherein the at least one gap (122) is from 0.05 microns to 100 microns at its largest dimension.

3. The cell culture sieve system (100) of claim 1, wherein the at least one gap (122) is 0.05, 0.1, 1, 10, 20, 30, 40, 50, 60, 70, 80, 90, or 100 microns at its largest dimension.

4. The cell culture sieve system (100) of claim 1, wherein the at least one gap (122) is from 0.05 to 10 microns, 10 to 50 microns, or 50 to 100 microns at its largest dimension.

5. The cell culture sieve system (100) of claim 1, wherein the culture substrate (105) is a part of a slide or plate.

6. The cell culture sieve system (100) of claim 1, wherein the cell culture sieve system (100) is part of a multi-well cell culture plate.

* * * * *